United States Patent
Caipa Campos et al.

(10) Patent No.: US 10,160,774 B2
(45) Date of Patent: Dec. 25, 2018

(54) PROCESS FOR THE PREPARATION OF TRIMETHYL METAL COMPOUNDS

(71) Applicant: Akzo Nobel Chemicals International B.V., Arnhem (NL)

(72) Inventors: Mabel Andrea Caipa Campos, Hengelo (NL); Glen Rosini, Saint Charles, IL (US); Richard Herman Woudenberg, Diepenveen (NL); Andy Kurniawan, Deventer (NL); Marcellinus Antonius Maria Te Nijenhuis, Warnsveld (NL)

(73) Assignee: AKZO NOBEL CHEMICALS INTERNATIONAL B.V., Arnhem (NL)

( * ) Notice: Subject to any disclaimer, the term of this patent is extended or adjusted under 35 U.S.C. 154(b) by 0 days.

(21) Appl. No.: 15/753,583

(22) PCT Filed: Aug. 25, 2016

(86) PCT No.: PCT/EP2016/070038
§ 371 (c)(1),
(2) Date: Feb. 20, 2018

(87) PCT Pub. No.: WO2017/036899
PCT Pub. Date: Mar. 9, 2017

(65) Prior Publication Data
US 2018/0244697 A1  Aug. 30, 2018

Related U.S. Application Data

(60) Provisional application No. 62/211,063, filed on Aug. 28, 2015.

(30) Foreign Application Priority Data

Oct. 2, 2015 (EP) .................................. 15188212

(51) Int. Cl.
*C07F 5/00* (2006.01)

(52) U.S. Cl.
CPC ...................................... *C07F 5/00* (2013.01)

(58) Field of Classification Search
None
See application file for complete search history.

(56) References Cited

FOREIGN PATENT DOCUMENTS

| EP | 1 489 085 A1 | 12/2004 |
|---|---|---|
| JP | S54-12326 A | 1/1979 |
| WO | 2017/036898 A1 | 3/2017 |

OTHER PUBLICATIONS

XP002755226—Database CA—Chemical Abstracts Service, Columbus, OH, 1979, Ida et al., "Trimethylgallium," retrieved from STN Database accession No. 1979:439641—Abstract.
XP002755227—Database WPI, Week 197910, 1979, Thomson Scientific, London, GB, AN 1979-19025B, Jan. 30, 1979.
Notification of Transmittal of the International Search Report and the Written Opinion of the International Searching Authority, or the Declaration from the International Bureau of WIPO for International Application No. PCT/EP2016/070038, dated Sep. 22, 2016.

*Primary Examiner* — Clinton A Brooks
(74) *Attorney, Agent, or Firm* — Matthew D. Kellam

(57) ABSTRACT

Process for the production of a trimethyl metal compound with the formula $M(CH_3)_3$, said process comprising the steps of (i) reacting a metal trihalide $MX_3$ with a trialkyl aluminium compound $Al(R)_3$ to form a trialkyl metal compound $M(R)3$ and a dialkyl aluminium halide $Al(R)_2X$, and (ii) reacting said trialkyl metal compound $M(R)_3$ with either trimethyl aluminium $[Al(CH_3)_3]$ or dimethylaluminium halide $[Al(CH_3)_2X]$ to form said trimethyl metal compound $M(CH_3)_3$, wherein M is selected from the group consisting of Ga and In, X is a halogen, and R is a linear or branched alkyl group with 2 to 8 carbon atoms.

11 Claims, No Drawings

PROCESS FOR THE PREPARATION OF TRIMETHYL METAL COMPOUNDS

This application is a national stage filing under 35 U.S.C. § 371 of PCT/EP2016/070038, filed Aug. 25, 2016, which claims priority to U.S. Provisional Patent Application No. 62/211,063 filed Aug. 28, 2015, and European Patent Application No. 15188212.3, filed Oct. 2, 2015, the contents of which are each incorporated herein by reference in their entireties.

The present invention relates to a method for producing trimethyl metal compounds selected from trimethyl gallium and trimethyl indium.

With the advancement of mobile phones and optical communication technologies, demand is rapidly growing for compound semiconductors for use in high speed electronic devices such as high electron mobility transistors (HEMTs), heterojunction bipolar transistors (HBTs), semiconductor lasers, optical devices such as white and blue super high-intensity LEDs, and other applications.

In general, alkyl derivatives of group 12 and group 13 metals, and in particular the methyl or ethyl derivatives, are often used as metalorganic precursors for compound semiconductors. A great demand exists for, in particular, trimethyl gallium for the production of compound semiconductors by MOCVD with group 15 elements, such as nitrogen, arsenic, and the like.

Trimethyl gallium (TMG) is conventionally prepared by reacting a gallium trihalide (e.g. gallium trichloride) with trimethyl aluminium (TMAL). According to this reaction, the production of one mole of TMG requires the use of 3 moles of TMAL:

$$GaCl_3 + 3Al(CH_3)_3 \rightarrow Ga(CH_3)_3 + 3Al(CH_3)_2Cl$$

Trimethyl indium can be produced in comparable manner.

TMAL is considerably more expensive than other alkyl aluminum compounds, such as triethyl aluminium and dimethyl aluminium chloride.

With three moles of TMAL being required for the production of only one mole of TMG, it will be clear that the TMG production costs are heavily determined by the TMAL price.

One object of the present invention is therefore to provide a process for the production of trimethyl metal compounds, in particular trimethyl gallium and trimethyl indium, starting from the metal trihalides, that requires significantly less trimethyl aluminium or can be even absent of trimethyl aluminium. A further object is to perform such process in continuous mode or in a one-pot configuration.

These objects are achieved by the process of the present invention, which relates to the production of a trimethyl metal compound with the formula $M(CH_3)_3$, comprising the steps of (i) reacting a metal trihalide $MX_3$ with a trialkyl aluminium compound $Al(R)_3$ to form a trialkyl metal compound $M(R)_3$ and a dialkyl aluminium halide $Al(R)_2X$, and (ii) reacting said trialkyl metal compound $M(R)_3$ with either trimethyl aluminium $[Al(CH_3)_3]$ or dimethylaluminium halide $[Al(CH_3)_2X]$ to form said trimethyl metal compound $M(CH_3)_3$, As will be illustrated below, this process requires only one mole of TMAL per mole of produced trimethyl metal compound (if TMAL is used) and can even be performed in the complete absence of TMAL (if dimethylaluminium halide is used).

In a preferred embodiment, M is Ga.

In another preferred embodiment, the halide X is Cl, Br, or I, more preferably Cl or Br, and most preferably Cl.

Alkyl group R is preferably selected from ethyl and linear or branched propyl and butyl groups, including n-propyl, isopropyl, n-butyl, isobutyl, and tert-butyl. More preferably, the alkyl group is selected from ethyl, n-propyl, n-butyl, and isobutyl. Most preferably, the alkyl group R is ethyl.

According to the present process, step (i) involves the reaction between metal trihalide $MX_3$ and trialkyl aluminium $Al(R)_3$ to form a trialkyl metal of formula $M(R)_3$ and a dialkyl aluminium halide of formula $Al(R)_2X$.

M is preferably Ga and the halide X is preferably Cl, Br, or I, more preferably Cl or Br, and most preferably Cl. The metal trihalide is most preferably gallium trichloride.

Reaction of step (i) is preferably conducted under inert (e.g. nitrogen) atmosphere at a temperature in the range 0-280° C., preferably 25-250° C., most preferably 50-175° C.

The temperature can be kept constant during the reaction, but may also gradually rise.

The reaction of step (i) is carried out by introducing the metal trihalide and the trialkyl aluminium compound $Al(R)_3$, and optionally a solvent into a reaction vessel or a distillation column, under inert gas atmosphere. The compounds can be added in any form and in any order.

In one embodiment, the trialkyl aluminium compound $Al(R)_3$ and the metal trihalide are introduced in a distillation column, either separately or as a pre-mix. Defining the bottom of the distillation column as positon 0 and the top of the distillation column as position 1, the compound is preferably dosed to said column at a position between 0.1 and 0.9, more preferably between 0.25 and 0.75, even more preferably between 0.25 and 0.50, and most preferably between 0.25 and 0.40. Compounds that are solid under the addition conditions (e.g. indium trichloride or gallium trichloride) may be added as such, but may also be added to the reactor dissolved in a solvent or in molten form. Addition as solution is especially preferred if the process is conducted in continuous manner. Examples of suitable solvents are saturated aliphatic hydrocarbons like pentane, hexane, heptane, octane, nonane, decane, undecane, and dodecane; saturated alicyclic hydrocarbons like cyclohexane and cycloheptane; and aromatic hydrocarbons like toluene, xylene, trimethylbenzene, ethylbenzene, ethyltoluene, and indene. Preferred solvents are those that are easily separable from the resulting trimethyl metal compound.

The reaction of step (i) most preferably involves the reaction between gallium trichloride and triethyl aluminium (TEAL) to form triethyl gallium (TEG) and diethyl aluminium chloride (DEAC):

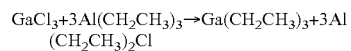

$$GaCl_3 + 3Al(CH_2CH_3)_3 \rightarrow Ga(CH_2CH_3)_3 + 3Al(CH_2CH_3)_2Cl$$

The trialkyl aluminium $Al(R)_3$ is preferably added to the metal trihalide $MX_3$ in a slight excess compared to the theoretical molar ratio of 3:1.

This excess is preferably 0-10 mol %, more preferably 0-5 mol %, and most preferably at most 0-3 mol %. The molar ratio $Al(R)_3:MX_3$ is therefore preferably 3.0:1-3.3:1, more preferably 3.0:1-3.2:1, and most preferably 3.0:1-3.1:1.

The trialkyl metal compound that is formed in step (i) is subsequently used in step (ii).

In step (ii), the trialkyl metal compound $M(R)_3$ is reacted with either dimethyl aluminium halide ($Al(CH_3)_2X$) or trimethyl aluminium (TMAL) to form the trimethyl metal compound $M(CH_3)_3$. Most preferably, the process involves the reaction between triethyl gallium (TEG) and either trimethyl aluminium (TMAL) or dimethyl aluminium chloride (DMAC) to form trimethyl gallium (TMG). The side products are either triethyl aluminium (TEAL) or diethyl aluminium chloride (DEAC):

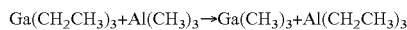

or

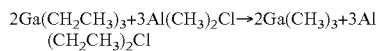

The advantage of a reaction with TMAL is that a trialkyl aluminium compound Al(R)$_3$ is formed as a side-product, which can be re-cycled to step (i). Furthermore, the above reaction schemes show that per mole TMG only one mole of TMAL is required, whereas the prior art process requires three moles of TMAL per mole of TMG. As explained above, TMAL is very expensive; much more than any other aluminium alkyl compound.

The advantage of the reaction with dimethyl aluminium halide is that it leads to a process that does not require any TMAL at all. Even the production of dimethyl aluminium halide does not require the use of TMAL, since it can simply be prepared from the raw materials aluminium powder, methyl chloride, and triethyl aluminium.

Step (ii) is preferably conducted under inert (e.g. nitrogen) atmosphere at a temperature in the range 0-280° C., preferably 25-250° C., most preferably 50-175° C.

The temperature can be kept constant during the reaction, but may also gradually rise.

The reaction can be performed at atmospheric pressure or lower pressures. At lower pressures, lower temperatures may be applied.

TMAL is preferably added to the trialkyl metal compound M(R)$_3$ in a slight excess compared to the theoretical molar ratio of 1:1. This excess is preferably 0-50 mol %, more preferably 0-25 mol %, and most preferably at most 0-10 mol %. The molar ratio TMAL:M(R)$_3$ is therefore preferably 1.0:1-1.5:1, more preferably 1.0:1-1.3:1, and most preferably 1.0:1-1.1:1.

Dimethylaluminium halide is preferably added to the trialkyl metal compound M(R)$_3$ in a slight excess compared to the theoretical molar ratio of 3:2. This excess is preferably 0-50 mol %, more preferably 0-25 mol %, and most preferably at most 0-10 mol %. The molar ratio dimethylaluminium halide:M(R)$_3$ is therefore preferably in the range 3.0:2-10.0:2. more preferably 3.0:2-8.0:2, more preferably 3.0:2-6.0:2, even more preferably 3.0:2-4.5:2, more preferably 3.0:2-3.8:2, and most preferably 3.0:2-3.3:2.

If desired, KF can be added to the reaction mixture in order to decompose any undesired aluminium complexes.

The reaction of step (ii) can be carried out by introducing the trialkyl metal compound M(R)$_3$, either dimethyl aluminium halide (Al(CH$_3$)$_2$X) or trimethyl aluminium (TMAL), and optionally a solvent into a reaction vessel or distillation column under inert gas atmosphere. These compounds can be added in any form and in any order.

In a preferred embodiment, the trialkyl metal compound M(R)$_3$ obtained in step (i) is introduced in a distillation column. The dimethyl aluminium halide (Al(CH$_3$)$_2$X) or trimethyl aluminium (TMAL) can also be introduced into the distillation column, but can also added to the re-boiler.

Defining the bottom of the distillation column as positon 0 and the top of the distillation column as position 1, the compound/compounds is/are preferably dosed to said column at a position between 0.1 and 0.9, more preferably between 0.25 and 0.75, even more preferably between 0.25 and 0.50, and most preferably between 0.25 and 0.40.

In a preferred embodiment, step (i) and step (ii) are each conducted in a distillation column, said columns being connected in series.

Assuming that the bottom of the distillation column is at positon 0 and the top of the distillation column as position 1, the trialkyl aluminium compound Al(R)$_3$, the metal trihalide, and the product of step (i) are preferably dosed to said columns at a position between 0.1 and 0.9, more preferably between 0.25 and 0.75, even more preferably between 0.25 and 0.50, and most preferably between 0.25 and 0.40.

In an alternative embodiment, both step (i) and step (ii) are performed in one single reactor (one pot reaction) by adding the required amounts of metal trihalide MX$_3$, trialkyl aluminium Al(R)$_3$, and trimethyl aluminium to a reactor and isolating the produced M(CH$_3$)$_3$ by distillation or crystallisation.

As mentioned above, the trialkyl aluminium Al(R)$_3$ side product that is formed may be re-cycled for use in step (i).

Examples of suitable solvents are saturated aliphatic hydrocarbons like pentane, hexane, heptane, octane, nonane, decane, undecane, and dodecane; saturated alicyclic hydrocarbons like cyclohexane and cycloheptane; and aromatic hydrocarbons like toluene, xylene, trimethylbenzene, ethylbenzene, ethyltoluene, and indene. Preferred solvents are those that are easily separable from the resulting trimethyl metal compound, more preferably by having a boiling point that differs significantly from that of the trimethyl metal compound.

The trimethyl gallium and trimethyl indium obtained by the process of the present invention can be suitably used for the preparation of semiconductor devices, e.g. gallium nitride-based semiconductors.

EXAMPLES

All experiments were carried out in a glovebox with nitrogen as a protective gas.

Example 1

One-Pot Synthesis of Trimethyl Gallium (TMG) from Gallium Trichloride, Triethylaluminum (TEAl), and Trimethyl Aluminium (TMAl)

17.60 g (0.100 mol, 1.0 eq.) of GaCl$_3$ (ex MCP) were poured into a 50 ml two-neck round-bottom flask equipped with a distillation column, stirrer and a thermocouple. 22.80 g (0.200 mol, 2 eq.) TEAL (>95% AkzoNobel) and 7.90 g (0.110 mol, 1.1 eq.) TMAL (98.5%, AkzoNobel) were mixed together and subsequently added dropwise to GaCl$_3$. The mixture was gradually heated to 160° C. The distillate was collected into a cooled receiving flask (−5° C.) with a top temperature of 56-61° C. TMG was isolated in a 78.1% yield (9.08 g, 0.079 mol) with a purity of 98% based on $^1$H NMR analysis.

Example 2

One-Pot Synthesis of Trimethyl Gallium (TMG) from Gallium Trichloride, Triethylaluminum (TEAL), and Dimethyl Aluminium Chloride (DMAC)

10.60 g (0.060 mol, 1.0 eq.) of GaCl$_3$ (ex MCP) were poured into a 50 ml two-neck round-bottom flask equipped with a distillation column, stirrer and a thermocouple. 20.60 g (0.200 mol, 3 eq.) TEAL (>95% AkzoNobel) and 9.20 g (0.10 mol, 1.66 eq.) DMAC (98.5%, AkzoNobel) were mixed together and subsequently added dropwise to GaCl$_3$.

The mixture was gradually heated to 160° C. The distillate was collected into a cooled receiving flask (−5° C.) with a top temperature of 56-61° C. TMG was isolated in a 50% yield (3.45 g, 0.030 mol) with a purity of 98.1% based on $^1$H NMR analysis.

Example 3

Step 1: Synthesis of Triethylgallium

In a 1 liter reactor with a 60 cm packed column, 390 g of triethylaluminum was added. The contents were cooled to 0° C. and solid gallium trichloride (198 g) was slowly added in portions (dosing time: 50 minutes). An exothermic reaction was observed.

The final solution, which was slightly grey, was heated and the formed triethylgallium was distilled off at 50 mbar. In total, 181 g of crude triethyl gallium was isolated. The purity was 98% (main impurity: diethylaluminum chloride). This material was used without further purification in the next step.

Step 2: Synthesis of Trimethylgallium

A reactor with a 60 cm packed column was filled with dimethylaluminum chloride (383 g). The dimethylaluminum chloride was heated to reflux.

At a height of 20 cm from the bottom of the packed column, triethylgallium (167 g) was introduced over 79 minutes. The ethyl-methyl exchange reaction occurred in the column and the formed trimethylgallium (bp. 56° C.) was distilled over the top of the column. In total, 126 g of distillate was isolated. Yield of trimethyl gallium: 96%: purity: 99.8%.

The invention claimed is:

1. Process for the production of a trimethyl metal compound with the formula $M(CH_3)_3$, said process comprising the steps of (i) reacting a metal trihalide $MX_3$ with a trialkyl aluminium compound $Al(R)_3$ to form a trialkyl metal compound $M(R)_3$ and a dialkyl aluminium halide $Al(R)_2X$, and (ii) reacting said trialkyl metal compound $M(R)_3$ with either trimethyl aluminium $[Al(CH_3)_3]$ or dimethylaluminium halide $[Al(CH_3)_2X]$ to form said trimethyl metal compound $M(CH_3)_3$, wherein M is selected from the group consisting of Ga and In, X is a halogen, and R is a linear or branched alkyl group with 2 to 8 carbon atoms.

2. Process according to claim 1 wherein the process is conducted as a one-pot reaction, in which the metal trihalide $MX_3$, the trialkyl aluminium $Al(R)_3$, and either trimethyl aluminium or dimethylaluminium halide are added to a reactor to form the trimethyl metal compound $M(CH_3)_3$.

3. Process according to claim 1, wherein steps (i) and (ii) are conducted in distillation columns, connected in series.

4. Process according to claim 1 wherein the reaction is performed in continuous mode.

5. Process according to claim 1 wherein M is Ga.

6. Process according to claim 1 wherein R is selected from the group consisting of ethyl and linear or branched propyl and butyl groups.

7. Process according to claim 6 wherein R is selected from the group consisting of ethyl, n-propyl, n-butyl, and isobutyl.

8. Process according to claim 7 wherein R is ethyl.

9. Process according to claim 1 wherein step (ii) involves the reaction of trialkyl metal compound $M(R)_3$ with trimethyl aluminium $(Al(CH_3)_3)$ to form the trimethyl metal compound $M(CH_3)_3$ and trialkyl aluminium $Al(R)_3$.

10. Process according to claim 9 wherein the produced trialkyl aluminium is recycled to step (i) for the production of the trialkyl metal compound $M(R)_3$.

11. Process according to claim 1 wherein the produced trimethyl metal compound $M(CH_3)_3$ is isolated from the reaction mixture by distillation or crystallisation.

* * * * *